(12) United States Patent
Abraham-Fuchs et al.

(10) Patent No.: US 7,890,340 B2
(45) Date of Patent: Feb. 15, 2011

(54) METHOD AND SYSTEM FOR ALLOWING A NEUROLOGICALLY DISEASED PATIENT TO SELF-MONITOR THE PATIENT'S ACTUAL STATE

(75) Inventors: Klaus Abraham-Fuchs, Erlangen (DE); Kai-Uwe Schmidt, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 3171 days.

(21) Appl. No.: 09/742,268

(22) Filed: Dec. 20, 2000

(65) Prior Publication Data

US 2004/0073452 A1    Apr. 15, 2004

(30) Foreign Application Priority Data

Dec. 20, 1999    (DE)    ................. 199 61 526

(51) Int. Cl.
*G06F 17/60*    (2006.01)
(52) U.S. Cl. ................. 705/2; 705/3; 128/899; 128/630; 600/25; 340/384.1
(58) Field of Classification Search ................. 705/2–3; 128/899, 630; 600/25; 340/384.1
See application file for complete search history.

(56) References Cited

U.S. PATENT DOCUMENTS

| 5,147,205 | A | * | 9/1992 | Gross et al. ................. 434/169 |
| 5,673,703 | A | * | 10/1997 | Fisher et al. ................. 600/552 |
| 5,772,585 | A | * | 6/1998 | Lavin et al. ................. 600/300 |
| 5,788,648 | A | * | 8/1998 | Nadel ................. 600/544 |
| 5,844,824 | A | * | 12/1998 | Newman et al. ................. 345/156 |
| 5,857,173 | A | * | 1/1999 | Beard et al. ................. 704/276 |
| 5,868,135 | A | * | 2/1999 | Kaufman et al. ................. 600/300 |
| 5,882,203 | A | * | 3/1999 | Correa et al. ................. 434/236 |
| 5,899,855 | A | * | 5/1999 | Brown ................. 600/301 |
| 5,941,829 | A | * | 8/1999 | Saltzstein et al. ................. 600/509 |
| 6,077,082 | A | * | 6/2000 | Gibson et al. ................. 434/262 |
| 6,149,585 | A | * | 11/2000 | Gray ................. 600/300 |
| 6,277,071 | B1 | * | 8/2001 | Hennessy et al. ................. 600/300 |
| 6,354,299 | B1 | * | 3/2002 | Fischell et al. ................. 128/899 |
| 2003/0145854 | A1 | * | 8/2003 | Hickle ................. 128/204.18 |

FOREIGN PATENT DOCUMENTS

WO    WO 99/23997    5/1999

OTHER PUBLICATIONS

"Forschung and Innovation", II/98, Verlag Siemens AG, Corporate Publishing Erlangen, pp. 18-22.
"Die Medizinische Versorgung Kommt Nach Hause," Pease, Forschung and Innovation (1998) pp. 18-22.

* cited by examiner

*Primary Examiner*—Vanel Frenel
(74) *Attorney, Agent, or Firm*—Alexander J Burke

(57) ABSTRACT

In a method for allowing a patient suffering from a neurological disease and being treated with medication to self-monitor his or her current state, information regarding the motor functions and/or verbal and/or cognitive abilities of the patient are interactively acquired upon using a computer located for easy and repeated access by the patient, and at least one criterion number or a statement describing the state is determined on the basis of this information by an expert system at the computer and is made available to the patient by an output device at the computer.

26 Claims, 1 Drawing Sheet

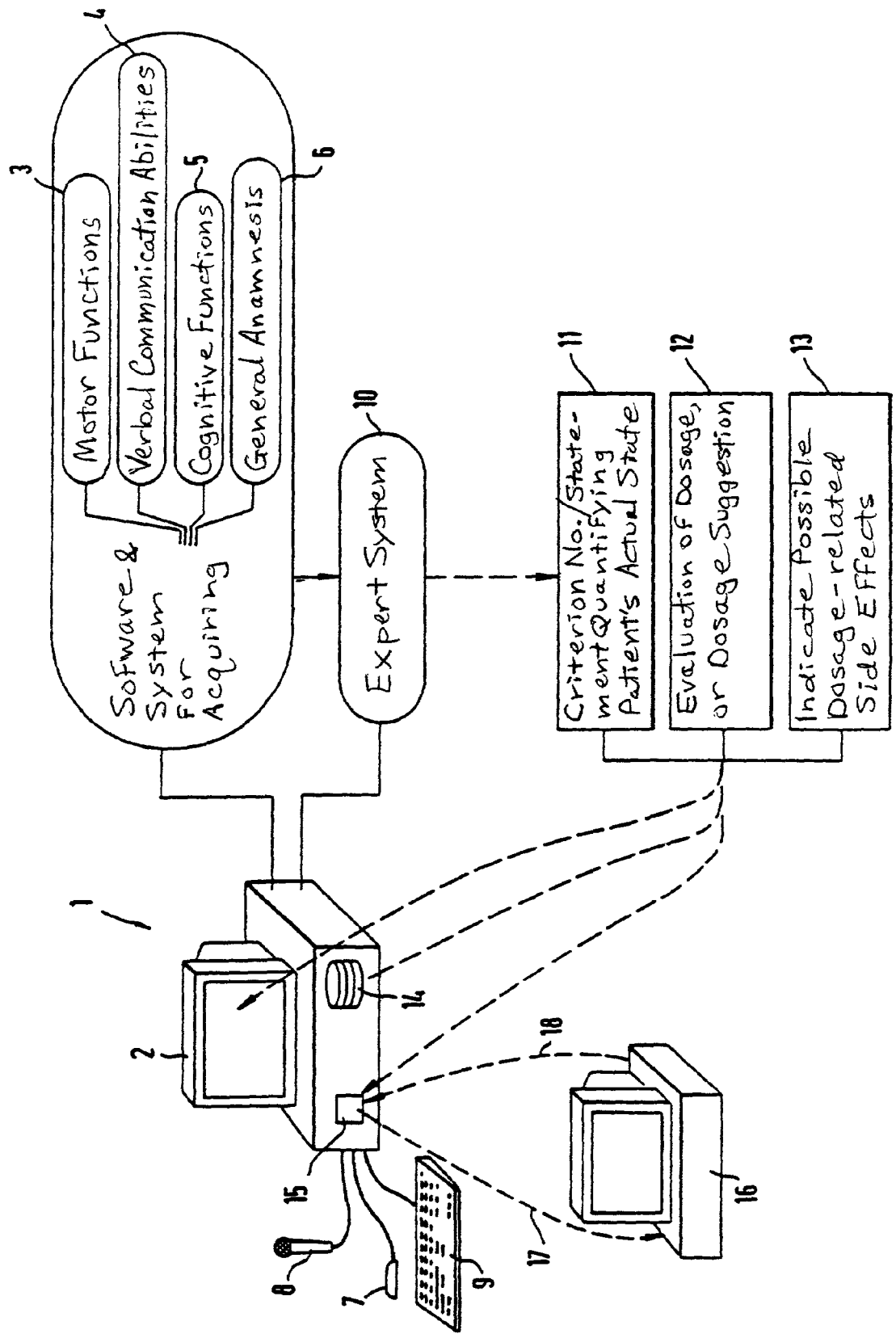

METHOD AND SYSTEM FOR ALLOWING A NEUROLOGICALLY DISEASED PATIENT TO SELF-MONITOR THE PATIENT'S ACTUAL STATE

BACKGROUND OF THE INVENTION

1. Field of the Invention

The present invention relates to a method for a patient, who suffers from a neurological disease which is treated with medication, to self-monitor his or her current state.

2. Description of the Prior Art

Patients having neurological or psychiatric diseases are frequently treated over a long period of time with medications (such as psychopharmaceutical medication from the class of the neuroleptic agents), which negatively influence mental abilities such as reactivity, coordination, verbal articulation, memory, cognitive abilities etc. Diseases treated in this manner include epilepsy, depression, schizophrenia, sleep disturbances etc., for example. In such a medication therapy, the goal of the physician is to select the dosage and duration of the intake of the medication such that the negative effects of the disease are suppressed as much as possible (such as epileptic attacks) and such that the quality of life of the patient is impaired as little as possible as result of a restriction of the aforementioned natural abilities.

This balance between the desired effect and side effects of the medication is known as optimal medication adjustment. Particularly when the medication is taken over a long period of time (several weeks or months), the optimum dosage can continuously change, since the patient gets used to the medication or since the disease state can change, for example. Therefore, there is the need to have regular monitoring for optimizing the medication adjustment with respect to such long-time therapies. It is particularly desired that the effect of the medication is not monitored only sporadically by the physician during a visit of the patient in the practice, but rather that such monitoring ensues more frequently and primarily in the context of everyday living conditions at home.

If the side effects of the medication correlate with modifications of metabolic parameters, for example in the blood or urine, such a medication monitoring can be undertaken by monitoring laboratory measured values, but this is extremely complicated. If higher functions of the human organism, such as the cited neurological abilities, are influenced, however, the degree of influence can no longer be determined by simple laboratory measured values, electrophysiological measured values etc. It is instead necessary to assess the impaired neurological function of the patient per se.

The periodical "Forschung und Innovation", II/98, Verlag Siemens AG, Unternehmenskommunikation, Cooperate Publishing Erlangen, order No. A 19100-L 516-U 982, page 18-22 discloses a system which can query anamnesis data and which can provide an analysis of the state of health of a person. For example, this system is also capable of asking children to hit a tennis ball on a screen in order to alert the child's parents to potential neurological problems before they occur. It is also possible to carry out vision tests and hearing testes with the system. A real self-monitoring for the patient, which allows the patient to obtain a "snapshot" about his or her actual state, is not possible with this known system.

An object of the present invention is to provide a method and a system for implementing the method, so that a patient can obtain a current assessment about his or her actual state of health (at least as to the aforementioned cognitive and motor skills).

This object is achieved in accordance with the invention in a method for a patient to self-monitor his or her actual state, the patient suffering from a neurological disease which is treated with medication, wherein items of information regarding the motor functions, verbal and/or cognitive abilities of the patient are interactively acquired using a computer that is located for daily access by the patient, and wherein at least one self-monitoring number or statement describing the state is determined by an expert system on the basis of these items of information, and wherein the self-monitoring number or statement are emitted as an output to the patient by an output device at the computer device.

In the inventive method, the patient must interactively communicate with the computer device. Specific items of information, which represent or supply a self-monitoring for the momentary motor functions, verbal and/or cognitive abilities of the patient, are acquired by the computer and are processed in an expert system, which can be fashioned as a neural network, for example, in order to quantify the state of the patient concerning his or her motor/verbal/cognitive abilities. The result of the processing in the expert system is a self-monitoring number describing the state (for example a number from the range 0-100, whereby "0" stands for a very bad state and "100" for a very good state) or can be a statement providing the patient with information about his or her actual state. On the basis of the determined self-monitoring number or the statement, the patient can recognize his or her actual state, potentially by comparing it with a self-monitoring number or statement determined during the last monitoring, so that the patient can react appropriately. The reaction can be of different types. The reaction may be to do nothing, for example to maintain the current medication dosage if the state has not worsened or improved. A reaction of the patient can be an increase of the medication dosing when his or her state has worsened, for example, or if the last increase has not taken effect, or the reaction can be a reduction of the dosage if a clear improvement can be seen compared to the last state assessment or the last state assessments.

The inventive method enables the patient to simply receive items of information about his or her actual state, so that the patient can gain knowledge about his or her state or state of health arbitrarily short at times separated by intervals. Otherwise, a visit to the doctor would be necessary and such visits are separated by relatively long time intervals. Moreover, a physician need not be consulted when the examination result indicates an improvement of the state, or stability.

In an embodiment of the invention, the patient carries out software-controlled motor function test exercises at the computer in order to acquire items of information characterizing motor functions. Such motor function test exercises serve the purpose of allowing the negative and/or the positive effects of a medication dosage on the state of the patient to be identified, and on the basis of which an information value quantifying the negative and/or positive effects is determined. An expert system processes this information value.

The patient is requested to carry out corresponding motor function test exercises by means of suitable software stored at the computer, with the motor function test exercises being displayed at a monitor in the form of a computer game, for example.

For example, these exercises can be reaction exercises or positioning exercises in the framework of which the patient must move among specific prescribed positions by means of a cursor shown at the screen, for example, by using an operating mouse or a similar input device requiring a certain dexterity. All exercises that challenge the motor function of the patient in any form or other and that are useful for acquiring information can be utilized. The test exercises can be specifically structured such that they serve the purpose of concretely determining negative or positive effects. The information value can be determined by the software program itself, which controls the test exercises; alternatively, separate suitable software can be stored therefor. It is possible to directly give the information as raw data to the expert system, which carries out a direct processing resulting in emission of the cited quantifying information value.

Alternatively or in addition, a speech assessment system, which is stored in the computer, can be utilized for acquiring items of information with respect to the verbal abilities of the patient. Such a speech assessment system can contain speech recognition algorithms and/or a phonetic data bank, so that an information value of the articulation ability, which quantifies the negative and/or positive effects of a medication dosing, is determined, which can be further processed by the expert system. The speech assessment system can play prescribed sentences to the patient, which the patient must repeat. This is recorded by a speech recording device and is evaluated using speech recognition algorithms, or the phonetic databank, and a quantitative information value is determined. In the framework of this determination, for example, the speed of the word sequence spoken by the patient is used, as is the exactness of the pronunciation and the accentuation etc. It is also possible for the expert system to directly further processed the recorded items of information subsequent to a first assessment by the speech assessment system, without determining an information value.

In order to finally evaluate the cognitive abilities, questions, which are prescribed in a software-controlled manner in a question-response technique, can be optically or acoustically supplied to the patient in a further embodiment of the invention. The patient must verbally or manually answer these questions from the computer. On the basis of the responses, an information value of the cognitive abilities, which quantifies the negative and/or positive effects, is determined. An expert system further processes this information value. The questions for the patient can be arbitrary knowledge questions, which are dependent on the degree of education of the patient, and on the clinical state of the patient, in terms of their degree of difficulty.

In a further embodiment of the invention, items of information can be entered at the computer or can be verbally acquired in addition to the aforementioned items of information using an acquisition system. These items of information relate to the subjective state of health of the patient and which are further processed by the expert system. Such data are general anamnesis data. In order to obtain such data, prescribed questionnaires, for example, are stored in the form of a suitable software program, and the questionnaires are visualized for the patient at the screen and the patient must answer or fill out these questionnaires. Knowledge-based dialog systems etc. are also useable.

In general, the information used in the inventive method is always acquired using appropriate software programs. The expert system is capable of deriving a corresponding criterion number or statement, which informs the patient about his or her actual state, from the sum of the acquired items of information or exercise results, as well as from the acquired verbal information. Expediently, the derived criterion numbers or statements can be stored and successive numbers or statements can be represented with respect to time, so that long-term trend conclusions about the development of the state of the patient can be made.

It has proven to be expedient for the expert system to perform or output an evaluation regarding the medication dosage on the basis of the resulting criterion number or statement or the items of information, or on the basis of the determined information values. According to this inventive embodiment, the expert system is designed such that it supplies, on the basis of the given data, a suggestion concerning the medication dosage as to whether it is correct, too low or too high, so that the patient receives a first indication therefrom as to how he or she should act in the future. The determination of the evaluation can ensue on the basis of one criterion number or statement, which has been previously determined in the framework of the control session, if it is sufficient with respect to its information content to enable a well-grounded and expedient evaluation. It is particularly expedient for criterion numbers/statements, which have been registered earlier, to also be taken into consideration for determining the evaluation and to analyze the chronological curve or the modification on the part of the expert system, and for the evaluation ensues to be based on the analysis result. Even the chronological curve can disclose important information, which should be a part of a useful evaluation. For monitoring purposes, it is also expedient for the chronological curve of the criterion numbers to be represented at the output device, since the patient can quickly recognize the therapy success.

Apart from the fact that the patient can receive a sufficiently reliable overview about his or her actual state in a simple and fast manner, it would also be advantageous for the treating physician to receive this information as well. For this purpose, it can be inventively provided to transfer the criterion number or the statement, potentially also the evaluation regarding the medication dosage and potentially the items of information themselves, to the physician via a communication connection and with display there at a display device, such as a monitor. Thus, the physician can telemedically monitor the course and the patient can be better assessed and consulted at the next visit. If the physician, on the basis of the given criterion numbers/statements etc., prepares a diagnosis that requires action, the physician take immediate action if necessary. In addition, the physician can evaluate the state of the patient via the communication connection by examinings the transferred criterion numbers or statements and can transmit therapy instructions to the patient, which are shown to the patient at the output medium. It is thus possible to promptly get in contact with the patient and to potentially transmit important therapy instructions and measures. It is expedient for the data to be automatically transmitted to the physician during the acquisition of the patient information, or immediately after the criterion numbers or statements have been determined, so that it is assured that the physician, in fact, receives the bits of information and so that the patient is not responsible for the transmission, since the patient may not be able to do this task.

In addition to the method, the invention also relates to a system for implementing the method, having a computer that is arranged for easy access by the patient, with one or more software programs stored therein, with which test exercises with respect to the motor functions, verbal and/or cognitive abilities of the patient can be optically or acoustically made available to the patient, in an interactive fashion, at one or more output devices. The computer device is designed for acquiring the answer information from the patient, and an expert system is provided at the computer, which is designed for determining at least one criterion number or statement, which can be emitted at an output device and which describes the state of the patient, on the basis of the answer information. Therefore, suitable software programs, which serve the purpose of providing corresponding test exercises with respect to the motor functions, verbal and cognitive abilities of the patient, are stored at the part of the computer device. The output can ensue at a monitor can or acoustically. Furthermore, the computer means is designed for registering corresponding response reactions of the patient, i.e., the motor function-motion patterns are acquired at the software side as a reaction to the emitted motor function-test exercise; the verbal abilities and suchlike can be evaluated by a speech assessment system. The stored expert system serves the purpose of processing items of information in order to determine a criterion number or a statement based thereon, which describes the state of the patient in a quantified manner. An acquisition system for items of information that are to be acquired in the question-answer method, and that relate to the subjective state of health of the patient, can be incorporated as a part of the computer, or a separate acquisition system can be provided for this purpose. These data are also taken into consideration by the expert system.

The expert system itself is designed for determining the described criterion number or statement and is also designed for determining an evaluation with respect to a medication dosage on the basis of the acquired answer information or the determined information values or, respectively, the determined criterion number or statement. For this purpose, the expert system is expediently fashioned for analyzing the chronological curve or the modifications of the criterion numbers or statement, which can be stored therefor in a memory accessible by the computer, whereby the expert system prepares the evaluation upon consideration of the analysis result. Expediently, the information values and their evaluation results can be stored in order to enable long-term curve controls to be determined therefrom as well. Generally, all cited "parameters"—as far as they are stored—can be emitted at the output medium in the form of time-related curve diagrams.

A, transmission arrangement can be provided for transmitting the criterion number or statement, and possibly the evaluation regarding the medication dosage and possibly the information itself, via a communication connection to an external computer. The patient-operated computer can be fashioned for automatically transmitting to a fixed external computer means.

DESCRIPTION OF THE DRAWINGS

The FIGURE shows a schematic diagram of the inventive system and for describing the inventive method.

DESCRIPTION OF THE PREFERRED EMBODIMENTS

A computer 1 is shown with an output device 2 in the form of a monitor. Various software programs and systems for acquiring different bits of information are deposited on the part of the computer 1, so that it is possible to assess the actual state of a patient suffering from a neurological disease such as epilepsy. Suitable software and a suitable system for acquiring motor functions 3, for acquiring verbal-communication abilities 4, for acquiring cognitive abilities 5 and for acquiring general anamnesis data 6 reproducing the subjective state of health of the patient are stored in a memory accessibly by the computer 1. For example, computer game-like tasks, which must be solved by the patient, are presented to the patient at the monitor 2 for acquiring the motor functions. For example, these can be reaction exercises and such. In order to carry out the tasks or exercises, an operating mouse 7 is provided, for example, with which a cursor or other indicator can be moved across the monitor 2, and with which, for example, a fixed line, a moving point, etc. must be followed.

As already described, corresponding software and a system for acquiring the verbal-communicative abilities are stored. The system is a speech assessment system containing speech recognition algorithms and an appropriate phonetic data bank. Preprogrammed speech examples can be emitted via a loudspeaker (not shown in greater detail here) by means of this system. The patient must repeat the prescribed speech examples. A microphone 8 is provided for this purpose. The patient's repeated words/sentences are recorded and are processed by the software or speech assessment system. For this purpose, a suitable comparison step and a speech recognition step are provided, which analyze and evaluate the repeated words/sentences.

Furthermore, software and a system for acquiring cognitive abilities are provided. The patient can be asked questions via the monitor 2, which the patient must answer. For example, a keyboard 9 or also an operating mouse 7 can be utilized for entering answers.

Suitable software and a system for acquiring general anamnesis data such as the patient's momentary condition, currently manifested difficulties or problems of any kind, etc. can be provided. For this purpose, appropriate questionnaires or knowledge-based dialog systems are provided by means of the software. This dialog system can present corresponding questions at the monitor 2, which must then be answered by the patient using the operating mouse 7, the keyboard 9 or the microphone 8, for example.

All items of information that are registered by the computer 1 via the corresponding input units are preprocessed by the software or system and are forwarded to an expert system 10, which is installed at the computer 1. The expert system 10 can be a learning (trainable) neural network, for example. On the basis of all items of information supplied to the expert system 10, it determines a criterion number or statement 11 representing a quantified measure for the actual state of the patient. Furthermore, the expert system is fashioned for determining an evaluation 12 with respect to the dosage or for preparing a dosage suggestion. By means of the expert system 10, it is thereby determined whether the state of the patient has improved or worsened or whether it remained stable. After this result has been acquired, the expert system 10 evaluates whether the dosage is correct, too low or too high. A dosage suggestion can be prepared at the same time. The expert system also is designed for determining a statement 13 with respect to possible side effects of a new dosage or potentially of the same dosage.

All criterion numbers, statements and evaluations determined in the steps 11, 12 and 13 by the expert system are visualized for the patient at the output device 2, so that the patient, after the tests, or the information acquisitions have been completed, immediately gains knowledge about the evaluation result on the part of the expert system 10. Furthermore, at least the criterion number/statement 11, and possibly all other evaluations/statements, are transferred into and stored in memory 14 accessible by the computer 1. On the basis of the criterion numbers/statements etc. stored in the memory 14 over a period of time, monitoring of the treatment regimen can be undertaken, from which the chronological curve and trend of the therapy can be recognized. The dosage evaluation also can ensue on the basis of an analysis of the chronological course/trend of the criterion numbers, with the expert system 10 being designed for analyzing the stored earlier criterion numbers/statements.

The criterion numbers/statements/evaluations determined by the expert system 10 can be transmitted via a transmission arrangement 15, which is provided as part of the computer 1 and which is connected to a telecommunication line (not shown in greater detail), to an external computer 16 situated at the treating physician (arrow 17). The physician is thus informed about the monitoring result or evaluation result. After the physician has examined this information, the physician can send a response via the telecommunication network to the patient, with this response being visualized for said patient at the output device 2 (as indicated by arrow 18).

On the basis of an example, the functioning of the system is explained in greater detail:

A patient is suffering from a form of epilepsy, and the epileptic attacks can be generally suppressed by means of medication. As negative side effects of the attack suppression, however, the medication simultaneously slows down the reactivity of the patient and the patient's articulation ability, i.e. the speech sounds somewhat drawled and slow; sentence pauses occur frequently. It is important with respect to the optimization of the medication adjustment to keep these neurological deficits as low as possible. Although the patient typically immediately notices an increase in attack frequency and then either increases the medication dosing or consults a physician, the patient cannot subjectively assess impairments of the aforementioned abilities very well, and so the patient frequently does not notice a slow worsening.

On the basis of the inventive system, the patient can execute the test programs at the computer 1 at home, typically approximately every other day or only once per week. The patient's reaction speed is acquired and quantified in the above-described manner with the aid of computer game-like tests. Additionally, a speech assessments system wherein texts are read, repeated, questions from the computer means are answered etc., measures the articulation ability using speech recognition algorithms. Targeted to the epileptic person, general anamnesis, data can be acquired via "intelligent questionnaires" by the computer in the framework of an interactive dialog, for example "Do you have sleep disturbances?", "Do you have a headache?", "Do you have a feeling of nausea?", "Do you feel good or bad?" etc. The evaluation of the tests and the general anamnesis data, using the expert system 10, allows a statement as to whether the impairment as a result of medication side effects is stable as a trend, or whether it has become better or worse. Questions regarding the frequency and intensity of epileptic attacks also can be asked within the test period. The expert system can derive corresponding evaluations/statements such as "state of health o.k.", "Next test recommended in x-days", "Your reactivity has clearly worsened, lower the dose of the medication x to y and repeat the test in n-days" etc.

Although various minor modifications might be suggested by those skilled in the art, it should be understood that our wish to embody within the scope of the patent warranted hereon all such modifications as reasonably and properly come with the scope of our contribution to the art.

We claim as our invention:

1. A method for allowing a patient, suffering from a neurological disease and receiving medication for said disease, to self-monitor the patient's actual state, comprising the steps of:
providing a computer at a location readily accessible to a patient substantially on a daily basis for acquiring information from a patient;
acquiring information, via an interactive procedure, from a patient wherein the acquired information is selected from a group consisting of information characterizing a motor function of the patient, information characterizing a verbal communication ability of the patient, and information characterizing cognitive abilities of the patient;
providing an expert system accessible by the computer;
providing said acquired patient information to said expert system for processing thereby, and determining, from the acquired information, at least one quantified indicator describing the state of the patient suffering from a neurological disease which is treated with medication; and
providing said computer with an output device and making said quantified indicator available to the patient via said output device wherein said information comprises information characterizing a motor function of said patient, and wherein the step of acquiring information comprises conducting software-controlled motor function exercises for quantifying at least one of neutral, negative and positive effects of said medication on said patient's state, and quantifying said negative and positive effects for processing by said expert system for use in determining said quantified indicator.

2. A method as claimed in claim 1 wherein said information is information characterizing a verbal communication ability of said patient, and wherein the step of acquiring information comprises acoustically acquiring speech from said patient and assessing said speech with a speech assessment system having speech recognition algorithms and a phonetic data bank to obtain an information value quantifying at least one of neutral, negative and positive effects of said medication on said speech, and supplying said information value to said expert system for processing by said expert system for use in determining said quantified indicator.

3. A method as claimed in claim 1 comprising the step of entering additional information characterizing a subjective state of health of said patient during said step of acquiring information.

4. A method as claimed in claim 1 further comprising the step of obtaining a quantified information value representing said information acquired in said, step of acquiring and storing, after each interactive procedure, as stored information with respect to time, at least one of said quantified indicator, said acquired information and said quantified information value.

5. A method as claimed in claim 4 comprising providing said stored information to said expert system for producing an evaluation regarding dosage of said medication based on said stored information and making said evaluation available to the patient at said output device.

6. A method as claimed in claim 5 wherein said stored information includes said quantified indicator, and wherein said expert system produces said evaluation from a chronological analysis of a curve relative to time of the respective quantified indicators obtained after each interactive procedure.

7. A method as claimed in claim 6 further comprising the step of establishing communication between said computer and a physician located remote from said computer, and informing said physician of at least one of said quantified indicator, and said evaluation and said information, as transmitted information.

8. A method as claimed in claim 7 further comprising the step of transmitting therapy instructions from said physician to said computer based on an examination of said transmitted information, and making said therapy instructions available to the patient at said output device.

9. A method as claimed in claim 5 further comprising the step of making the chronological curve available to said patient as a displayed curve at said output device.

10. A method as claimed in claim 5 further comprising the step of storing said produced evaluation in a memory accessible by said computer.

11. A method as claimed in claim 1 wherein said step of determining further comprises formulating said quantified indicator as a number.

12. A method as claimed in claim 1 wherein said step of determining further comprises formulating said quantified indicator as a statement.

13. A method for allowing a patient, suffering from a neurological disease and receiving medication for said disease, to self-monitor the patient's actual state, comprising the steps of:
   providing a computer at a location readily accessible to a patient substantially on a daily basis for acquiring information from a patient;
   acquiring information, via an interactive procedure from a patient wherein the acquired information is selected from a group consisting of information characterizing a motor function of the patient, information characterizing a verbal communication ability of the patient, and information characterizing cognitive abilities of the patient;
   providing an expert system accessible by the computer;
   providing said acquired patient information to said expert system for processing thereby, and determining, from the acquired information, at least one quantified indicator describing the state of the patient suffering from a neurological disease which is treated with medication; and
   providing said computer with an output device and making said quantified indicator available to the patient via said output device wherein the step of acquiring information comprises generating questions requiring a response from said patient to the respective questions and, from said responses, generating an information value quantifying at least one of neutral, negative and positive effects of said medication on said cognitive abilities of the patient, and supplying said information value to said expert system for processing for use in determining said quantified indicator.

14. A method as claimed in claim 13 comprising the step of acoustically entering said responses from said patient into said computer.

15. A method as claimed in claim 13 comprising the step of manually entering said responses from said patient into said computer.

16. A system for allowing a patient suffering from a neurological disease and receiving medication for treating said disease, to self-monitor a state of the patient, comprising:
   a computer readily accessible by the patient disposed at a location at which said patient is present substantially on a daily basis;
   at least one software program installed in said computer able to execute an interactive procedure with said patient to obtain information selected from the group consisting of information characterizing a motor function of the patient, information characterizing verbal communication abilities of the patient, and information characterizing cognitive abilities of the patient;
   an input unit connected to said computer for use by said patient during said interactive procedure for acquiring said information;
   an expert system accessible by said computer able to receive said information and produce a quantified indicator from said information and making said quantified indicator available to said computer; and
   an output unit connected to said computer for providing said quantified indicator to the patient wherein said information is information characterizing verbal communication abilities of the patient, and wherein said input unit is an acoustical input unit, and wherein said software program assesses speech made by said patient into said input unit using speech algorithms and a phonetic data bank, and produces a quantified information value representing said verbal communication abilities, and makes said quantified information value available to said expert system.

17. A system as claimed in claim 16 wherein said information is information characterizing a motor function of the patient, and wherein said input unit is a manually operated input unit, and wherein said software program operates said computer to execute motor function test exercises and produces a quantified information value quantifying at least one of neutral, negative and positive effects of said medication on said motor function and makes said quantified information value available to said expert system.

18. A system as claimed in claim 16 wherein said information is information characterizing cognitive abilities of the patient and wherein said software operates said computer to present questions to said patient and to receive responses from said patient, and produces a quantified information value from said responses quantifying at least one of neutral, negative and positive effects of said medication on said cognitive abilities, and makes said quantified information value available to said expert system.

19. A system as claimed in claim 16 comprising a further software program for operating said computer to obtain additional information from said patient characterizing a subjective state of health of said patient.

20. A system as claimed in claim 16 wherein said software program in each interactive procedure produces a quantified information value from said information, and further comprising a memory accessible by said computer and by said expert system for storing, as stored information relative to time, at least one of said quantified indicator, said information and said quantified information value after each interactive procedure.

21. A system as claimed in claim 16 wherein said software operates said computer to formulate said quantified indicator as a number.

22. A system as claimed in claim 16 wherein said software operates said computer to formulate said quantified indicator as a statement.

23. A system for allowing a patient suffering from a neurological disease and receiving medication for treating said disease, to self-monitor a state of the patient, comprising:
   a computer readily accessible by the patient disposed at a location at which said patient is present substantially on a daily basis;
   at least one software program installed in said computer able to execute an interactive procedure with said patient to obtain information selected from the group consisting of information characterizing a motor function of the patient, information characterizing verbal communication abilities of the patient, and information characterizing cognitive abilities of the patient;
   an input unit connected to said computer for use by said patient during said interactive procedure for acquiring said information;

an expert system accessible by said computer able to receive said information and produce a quantified indicator from said information and making said quantified indicator available to said computer; and an output unit connected to said computer for providing said quantified indicator to the patient wherein said software program in each interactive procedure produces a quantified information value from said information, and further comprising a memory accessible by said computer and by said expert system for storing, as stored information relative to time, at least one of said quantified indicator, said information and said quantified information value after each interactive procedure and said expert system produces an evaluation from said stored information with regard to a dosage of said medication.

24. A system as claimed in claim 23 wherein said stored information includes said quantified indicator, and wherein said expert system produces said evaluation by analyzing a chronological curve of respective quantified indicators obtained from successive interactive procedures.

25. A system as claimed in claim 24 wherein said computer provides said chronological curve to said output device as a displayed curve.

26. A system as claimed in claim 23 further comprising a transmission link from said computer to an external computer located remotely from said computer for transmitting at least one of said evaluation and said quantified indicator to said external computer.

* * * * *